(12) United States Patent
Kushida et al.

(10) Patent No.: US 7,923,563 B2
(45) Date of Patent: Apr. 12, 2011

(54) AMORPHOUS OBJECT OF CINNAMIDE COMPOUND

(75) Inventors: Ikuo Kushida, Tsukuba (JP); Eriko Doi, Tsukuba (JP); Koichi Ito, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 982 days.

(21) Appl. No.: 11/663,550

(22) PCT Filed: Oct. 25, 2005

(86) PCT No.: PCT/JP2005/019626
§ 371 (c)(1),
(2), (4) Date: Mar. 23, 2007

(87) PCT Pub. No.: WO2006/046575
PCT Pub. Date: May 4, 2006

(65) Prior Publication Data
US 2009/0203916 A1 Aug. 13, 2009

(30) Foreign Application Priority Data
Oct. 26, 2004 (JP) ................. 2004-310909

(51) Int. Cl.
C07D 401/06 (2006.01)
(52) U.S. Cl. ........................................ 546/210
(58) Field of Classification Search ............ 546/210
See application file for complete search history.

(56) References Cited

U.S. PATENT DOCUMENTS

| | | | |
|---|---|---|---|
| 3,470,167 A | 9/1969 | Sarkar | |
| 3,989,816 A | 11/1976 | Rajadhyaksha | |
| 4,910,200 A | 3/1990 | Curtze et al. | |
| 4,910,220 A | 3/1990 | Braga | |
| 5,281,626 A | 1/1994 | Oinuma et al. | |
| 5,563,162 A | 10/1996 | Oku et al. | |
| 5,804,577 A | 9/1998 | Hebeisen et al. | |
| 5,985,856 A | 11/1999 | Stella et al. | |
| 6,235,728 B1 | 5/2001 | Golik et al. | |
| 6,306,870 B1 | 10/2001 | Bombrun et al. | |
| 7,053,087 B1 | 5/2006 | Beatch et al. | |
| 7,138,414 B2 | 11/2006 | Schoenafinger et al. | |
| 7,300,936 B2 | 11/2007 | Parker et al. | |
| 7,314,940 B2 | 1/2008 | Graczyk et al. | |
| 7,618,960 B2 | 11/2009 | Kimura et al. | |
| 7,667,041 B2 * | 2/2010 | Kimura et al. | 546/210 |
| 2001/0051642 A1 | 12/2001 | Ahn | |
| 2002/0128263 A1 | 9/2002 | Mutel et al. | |
| 2002/0183324 A1 | 12/2002 | Jacobson et al. | |
| 2003/0195201 A1 | 10/2003 | Bo et al. | |
| 2003/0208082 A1 | 11/2003 | Mutel et al. | |
| 2003/0225070 A1 | 12/2003 | Mutel et al. | |
| 2004/0006062 A1 | 1/2004 | Smallheer et al. | |
| 2004/0034096 A1 | 2/2004 | Jolidon et al. | |
| 2004/0038969 A1 | 2/2004 | Doherty et al. | |
| 2004/0063770 A1 | 4/2004 | Ahn et al. | |
| 2004/0087798 A1 | 5/2004 | Yamada | |
| 2004/0127494 A1 | 7/2004 | Parker et al. | |
| 2004/0127555 A1 | 7/2004 | Snow et al. | |
| 2004/0152743 A1 | 8/2004 | Schoenafinger et al. | |
| 2004/0192743 A1 | 9/2004 | Mjalli et al. | |
| 2004/0235864 A1 | 11/2004 | Graczyk et al. | |
| 2005/0070538 A1 | 3/2005 | Cheng et al. | |
| 2005/0131043 A1 | 6/2005 | Mutel et al. | |
| 2005/0187277 A1 | 8/2005 | Mjalli et al. | |
| 2006/0004013 A1 | 1/2006 | Kimura et al. | |
| 2007/0117798 A1 | 5/2007 | Kimura et al. | |
| 2007/0117839 A1 | 5/2007 | Kimura et al. | |
| 2007/0219181 A1 | 9/2007 | Kimura et al. | |
| 2007/0249833 A1 | 10/2007 | Cheng et al. | |
| 2008/0070902 A1 | 3/2008 | Kimura et al. | |
| 2008/0085894 A1 | 4/2008 | Parker et al. | |
| 2008/0096892 A1 | 4/2008 | Cheng et al. | |
| 2008/0280948 A1 | 11/2008 | Baumann et al. | |
| 2009/0048213 A1 | 2/2009 | Kimura et al. | |
| 2009/0048448 A1 | 2/2009 | Kushida et al. | |
| 2009/0203916 A1 | 8/2009 | Kushida et al. | |
| 2009/0270623 A1 | 10/2009 | Shimomura et al. | |

FOREIGN PATENT DOCUMENTS

| | | |
|---|---|---|
| CN | 1668593 A | 9/2005 |
| DE | 3 541 716 A1 | 5/1987 |
| EP | 0 219 756 A1 | 4/1987 |
| EP | 1 264 820 | 12/2002 |
| EP | 0 973 768 B1 | 7/2003 |
| EP | 1 757 591 A1 | 2/2007 |
| EP | 1 808 432 | 7/2007 |
| EP | 1 950 211 A1 | 7/2008 |
| EP | 1 953 151 A1 | 8/2008 |
| EP | 1 953 158 A1 | 8/2008 |
| GE | P 2006 3920 B | 5/2006 |

(Continued)

OTHER PUBLICATIONS

Borchardt et al. "Pharmaceutical profiling . . ." p. 93-125 (2004).*

(Continued)

*Primary Examiner* — Celia Chang
(74) *Attorney, Agent, or Firm* — Birch, Stewart, Kolasch & Birch, LLP

(57) ABSTRACT

An amorphous object of (3E)-1-[l(s)-1-(4-fluorophenyl) ethyl]-3-[3-methoxy-4-(4methyl-1H-imidazol-1-yl)benzylidene]piperidine-2-one, which is represented by the formula (1) and has Aβ-production inhibitory activity. The amorphous object has such satisfactory properties that it has excellent solubility, is stable, does not readily become a crystalline form, and has low hygroscopicity. It is hence suitable for use in pharmaceutical preparations.

4 Claims, 2 Drawing Sheets

FOREIGN PATENT DOCUMENTS

| | | | |
|---|---|---|---|
| GE | P-20084571 B | | 12/2008 |
| JP | 52-1035 | | 1/1977 |
| JP | 3-206042 | A | 9/1991 |
| JP | 8-283219 | A | 10/1996 |
| JP | 9-132578 | A | 5/1997 |
| JP | 10-510512 | A | 10/1998 |
| JP | 11-228548 | A | 8/1999 |
| JP | 11-513686 | A | 11/1999 |
| JP | 3176365 | B2 | 4/2001 |
| JP | 2001-508767 | A | 7/2001 |
| JP | 2001-527083 | A | 12/2001 |
| JP | 2003-206280 | A | 7/2003 |
| JP | 2004-520292 | A | 7/2004 |
| JP | 2004-531519 | A | 10/2004 |
| JP | 2004-536084 | A | 12/2004 |
| JP | 2005-72731 | A | 3/2005 |
| JP | 2005-518371 | A | 6/2005 |
| JP | 2005-526807 | A | 9/2005 |
| JP | 2005-531596 | A | 10/2005 |
| JP | 2005-533092 | A | 11/2005 |
| JP | 7-2780 | A | 12/2005 |
| JP | 2006-502247 | A | 1/2006 |
| JP | 2006-518738 | A | 8/2006 |
| JP | 2007-504282 | T | 3/2007 |
| JP | 2007-523903 | A | 8/2007 |
| RU | 2001126135 | A | 7/2003 |
| TW | 379224 | B | 1/2000 |
| TW | 200400824 | | 1/2004 |
| WO | WO-91/12237 | A1 | 8/1991 |
| WO | WO 95/21832 | A1 | 8/1995 |
| WO | WO-96/10559 | A1 | 4/1996 |
| WO | WO 97/14417 | A1 | 4/1997 |
| WO | WO-97/43287 | A1 | 11/1997 |
| WO | WO-98/03166 | A1 | 1/1998 |
| WO | WO9809963 | * | 3/1998 |
| WO | WO-98/24785 | A1 | 6/1998 |
| WO | WO-00/07993 | A1 | 2/2000 |
| WO | WO-00/50391 | A1 | 8/2000 |
| WO | WO-00/51981 | A1 | 9/2000 |
| WO | WO-01/68585 | A1 | 9/2001 |
| WO | WO-01/81312 | A2 | 11/2001 |
| WO | WO 03/027081 | A2 | 3/2003 |
| WO | WO-03/053912 | A1 | 7/2003 |
| WO | WO 03/074497 | A1 | 9/2003 |
| WO | WO-03/082292 | A1 | 10/2003 |
| WO | WO-03/101927 | A1 | 12/2003 |
| WO | WO 2004/002478 | A1 | 1/2004 |
| WO | WO-2004/007429 | | 1/2004 |
| WO | WO-2004/007455 | A1 | 1/2004 |
| WO | WO 2004/041776 | A2 | 5/2004 |
| WO | WO2004089868 | * | 10/2004 |
| WO | WO-2005/020921 | A2 | 3/2005 |
| WO | WO 2005/063754 | A1 | 7/2005 |
| WO | WO 2005/072731 | A1 | 8/2005 |
| WO | WO 2005/087767 | A1 | 9/2005 |
| WO | WO-2005/115990 | A1 | 12/2005 |
| WO | WO-2006/046575 | A1 | 5/2006 |
| WO | WO-2006/112550 | A2 | 10/2006 |
| WO | WO-2007/034282 | A2 | 3/2007 |
| WO | WO 2007/058304 | A1 | 5/2007 |
| WO | WO 2007/058305 | A1 | 5/2007 |
| WO | WO-2007/060810 | A1 | 5/2007 |
| WO | WO-2007/102580 | A1 | 9/2007 |
| WO | WO-2008/013213 | A1 | 1/2008 |
| WO | WO-2008/137139 | A1 | 11/2008 |
| WO | WO-2008/156580 | A1 | 12/2008 |
| WO | WO 2009/005729 | A1 | 1/2009 |
| WO | WO-2009/020580 | A1 | 2/2009 |

OTHER PUBLICATIONS

Lieberman "Pharmaceutical dosage forms" p. 462-465 (1990).*
Chen et al. "Preparation of cyclo . . ." Int. J. Pharm. v.242, p. 3-14 (2002).*
Guiroy, Acta Neuropathol (1991) 82:87-92.
Ross, J. Med. Chem., 1973, vol. 16, No. 4, 347-352.
Office Action dated Sep. 16, 2008, that issued in connection with copending U.S. Appl. No. 11/594,150.
Office Action dated Jul. 11, 2008, that issued in connection with copending U.S. Appl. No. 11/136,355.
Gong at al., PNAS, vol. 100, No. 18, pp. 10417-10422, (2003).
Hock et al., Neuron, vol. 38, No. 4, pp. 547-554, (2003).
Jarrett et al., Biochemistry, vol. 32, No. 18, pp. 4693-4697, (1993).
Glenner et al., Biochemical and Biophysical Research Communications; vol. 120, No. 3, p. 885-890, (1984).
Masters et al., Proc. Natl. Acad. Sci., vol. 82, No. 12, pp. 4245-4249, (1985).
Gouras et al., American Journal of Pathology, vol. 156, No. 1, pp. 15-20, (2000).
Scheuner et al., Nature Medicine, vol. 2, No. 8, pp. 864-870, (1996).
Forman et al., Journal of Biological Chemistry, vol. 272, No. 51, pp. 32247-32253, (1997).
Shearman et al., Biochemistry, vol. 39, No. 30, pp. 8698-8704, (2000).
Lewis et al., Biochemistry, vol. 42, No. 24, pp. 7580-7586, (2003).
Lewis et al., Biochemistry, vol. 42, pp. 7580-7586, (2003).
Lanz et al., vol. 309, No. 1, pp. 49-55, (2004).
Wong et al., Journal of Biological Chemistry, vol. 279, No. 13, pp. 12876-12882, (2004).
Blass et al., Journal of Neuroscience Research, vol. 66, No. 5, pp. 851-856, (2001).
Evin et al., Molecular Neuroscience, vol. 13, No. 5, pp. 719-723, (2002).
Yasuhara et al., Neuroscience Letters, vol. 171, Nos. 1 & 2, pp. 63-66, (1994).
Teller et al., Nature Medicine, vol. 2, No. 1, pp. 93-95, (1996).
Tokuda et al., Annals Neurology, vol. 41, No. 2, pp. 271-273, (1997).
Hayashi et al., Brain Research, vol. 789, No. 2, pp. 307-314, (1998).
Barelli et al., Molecular Medicine, vol. 3, No. 10, pp. 695-707, (1997).
Calhoun et al., PNAS, vol. 96, No. 24, pp. 14088-14093, (1999).
Dermaut et al., Brain, vol. 124, No. 12, pp. 2383-2392, (2001).
Cras et al., Acta Neuropathol, vol. 96, No. 3, pp. 253-260, (1998).
Herzig et al., Nature Neuroscience, vol. 7, No. 9, pp. 954-960, (2004).
Van Duinen et al., Proc. Natl. Acad. Sci., vol. 84, No. 16, pp. 5991-5994, (1987).
Levy et al., Science, vol. 248, No. 4959, pp. 1124-1126, (1990).
Laws et al., Neurobiology of Aging, vol. 23, No. 1, pp. 55-58, (2002).
Vaucher et al., Experimental Neurology, vol. 175, No. 2, pp. 398-406, (2002).
Morgan et al., Nature, vol. 408, No. 6815, pp. 982-985, (2000).
Moran et al., Proc. Natl. Acad. Sci., vol. 92, No. 12, pp. 5341-5345, (1995).
Koisinaho et al., PNAS, vol. 99, No. 3, pp. 1610-1615, (2002).
Zhang et al., Journal of Neuroscience, vol. 17, No. 20, pp. 7655-7661, (1997).
Sadowski et al., Neurochemical Research, vol. 29, No. 6, pp. 1257-1266, (2004).
O'Riordan et al., Neurology, vol. 59, No. 7, pp. 1108-1110, (2002).
Gehrmann et al., GLIA, vol. 15, No. 2, pp. 141-151, (1995).
Reynolds et al., Experimental Neurology, vol. 155, No. 1, pp. 31-41, (1999).
Smith et al., NeuroMolecular Medicine, vol. 4, Nos. 1 & 2, pp. 59-72, (2003).
Matsubara-Tsutsui et al., American Journal of Medical Genetics, vol. 114, No. 3, pp. 292-298, (2002).
Kirkitadze et al., Journal of Neuroscience Research, vol. 69, No. 5, pp. 567-577, (2002).
Evert et al., Journal of Neuroscience, vol. 21, No. 5, pp. 5389-5396, (2001).
Mann et al., Neuroscience Letters, vol. 109, Nos. 1 & 2, pp. 68-75, (1990).
Primavera et al., Journal of Alzheimer's Disease, vol. 1, No. 3, pp. 183-193, (1999).
Giasson et al., NeuroMolecular Medicine, vol. 4, Nos. 1 & 2, pp. 49-58, (2003).
Masliah et al., PNAS, vol. 98, No. 21, pp. 12245-12250, (2001).
Barrachina et al., Neurochemistry International, vol. 46, No. 3, pp. 253-260, (2005).
Schmidt et al., Acta Neuropathol, vol. 95, No. 2, pp. 117-122, (1998).

Ito et al., Neuropathology and Applied Neurobiology, vol. 17, No. 5, pp. 365-373, (1991).
Rosso et al., Annals of the New York Academy of Science, vol. 920, pp. 115-119, (2000).
Tolnay et al., Neuropathology and Applied Neurobiology, vol. 25, No. 4, pp. 295-305, (1999).
Jin et al., American Journal o Pathology, vol. 164, No. 3, pp. 975-985, (2004).
Sasaki et al., Acta Neuropathol., vol. 97, No. 5, pp. 463-468, (1999).
Tamaoka et al., J. Neurol., vol. 247, No. 8, pp. 633-635, (2000).
Hamilton et al., Acta Neuropathol, vol. 107, No. 6, pp. 515-522, (2004).
Turner et al., Neurochemical Research, vol. 29, No. 12, pp. 2281-2286, (2004).
Weller et al., Journal of Neuropathology and Experimental Neurology, vol. 57, No. 10, pp. 885-894, (1998).
Silverberg et al., The Lancet Neurology, vol. 2, No. 8, pp. 506-511, (2003).
Weller et al., Annals of the New York Academy of Science, vol. 903, pp. 110-117, (2000).
Yow et al., Neuropathology and Applied Neurology, vol. 28, pp. 149, (2002).
Weller et al., Annals of the New York Academy of Science, vol. 977, pp. 162-168, (2002).
Smith et al., Ann. Neural., vol. 49, No. 1, pp. 125-129, (2001).
Crook et al., Nature Medicine, vol. 4, No. 4, pp. 452-455, (1998).
Atwood et al., Brain Research Reviews, vol. 43, No. 1, pp. 164-178, (2003).
Lowenson et al., Trends in Cardiovascular Medicine, vol. 4, No. 1, pp. 3-8, (1994).
Singleton et al., Brain, vol. 123, No. 12, pp. 2467-2474, (2000).
Gattaz et al., J. Neural. Transm., vol. 111, No. 5, pp. 591-601, (2004).
Assini et al., Neurology, vol. 63, No. 5, pp. 828-831, (2004).
De Meyer et al., Circulation Research, vol. 90, No. 11, pp. 1197-1204, (2002).
Masahiko Kato et al., Chem. Pharm. Bull., 42 (12), 2546-2555 (1994).
Official Action dated Jul. 4, 2008, which issued in corresponding Russian Patent Application No. 2006146070.
Official Action issued on Nov. 14, 2008, in corresponding Russian Patent Application No. 2006146070.
T. A. Comery, The Journal of Neuroscience, Sep. 28, 2005, 25(39): 8898-8902.
T. A. Comely et al., Society for Neuroscience Annual Meeting (2003), Abstracts, Program No. 525.21.
J. G. Varnes et al., Bioorganic & Medicinal Chemistry Letters, 14 (2004) 1645-1649.
H. Stark et al., Pharamzie 52 (1997), vol. 6, pp. 419-423.
M. Kajbaf et al., Journal of Chromatography, 575 (1992) 75-85.
S. L. Marcus, Cancer Research, 45, 112-115, Jan. 1995.
H. L. Yale, J. Med. Chem., 1966, 9(1), 42-46.
S. M. Catalano et al., "The Role of Amyloid-Beta Derived Diffusible Ligands (ADDLs) in Alzheimer's Disease," Current Topics in Medicinal Chemistry, vol. 6, 597-608 (2006).
Search Report issued May 27, 2009, in connection with Georgia Patent Application No. AP 2006 010709 (with English translation).
The International Search Report for International Appl. No. PCT/JP2008/053887, mailed Sep. 19, 2008.
Office Action from Russian Patent Appl. No. 2008125426/04(030920), date Jun. 1, 2009.
Office Action from U.S. Appl. No. 11/715,440, dated Jul. 16, 2009.
Office Action from U.S. Appl. No. 12/200,731, dated Jul. 30, 2009.
Official Action issued Jan. 22, 2010, in Peruvian Patent Application No. 001480-2006.
Office Action issued Jan. 19, 2010, in copending U.S. Appl. No. 11/596,723.
Office Action issued Oct. 1, 2009, in Georgia Application No. 87447.
Tietze, Lutz Friedjan et al., "Detailed Organic Synthesis", Jikken Manual (Revised Second Edition) Nankodo Co., pp. 196-199, Jan. 15, 1995.
Brocchini, Stephen et al., "Preparation of piperazinedione-derivative inhibitors of plasminogen activator inhibitor". Database CA [Online] Chemical Abstracts Serivce, Columbus Ohio, US, XP002574973, pp. 1-2, Aug. 17, 1995.
Database Crossfire Beilstein, Beilstein Institut Zur Foerderung der Chemischen Wissenschaften, Frankfurt am Main, DE, XP002574972, 1 page, Aug. 11, 2005.
Supplementary European Search Report dated Apr. 7, 2010 in European Patent Application No. 05743758.4.
Eurasian Official Action, dated Mar. 12, 2010, for Eurasian Application No. 200870336/28.
Extended European Search Report, dated Apr. 24, 2009, for European Application No. 05805284.6.
Extended European Search Report, dated Aug. 4, 2010, for European Application No. 06822806.3.
Japanese Official Action, dated Sep. 28, 2007, for Japanese Application No. 2006-513906.
Pakistani Official Action, dated Apr. 11, 2008, for Pakistani Application No. 1435/2006.
Reynolds et al., "Myeloperoxidase Polymorphism is Associated with Gender Specific Risk for Alzheimer's Disease," Experimental Neurology, vol. 155, pp. 31-41, 1999.
Singapore Written Opinion, dated Feb. 11, 2009, for Singapore Application No. 0803266-6.
Singapore Written Opinion, dated Feb. 24, 2009, for Singapore Application No. 0803192-4.
US Office Action, dated Apr. 3, 2009, for U.S. Appl. No. 11/594,130.
US Office Action, dated Apr. 1, 2009, for U.S. Appl. No. 12/200,731.
US Notice of Allowance, dated Aug. 20, 2010, for U.S. Appl. No. 12/200,731.
Extended European Search Report, dated Apr. 23, 2010, for European Application No. 08752763.6.
International Preliminary Report on Patentability, dated Nov. 29, 2006, for Application No. PCT/JP2005/009537.
International Search Report, dated Feb. 24, 2009, for Application No. PCT/JP2009/051162.
International Search Report, dated Feb. 7, 2006, for Application No. PCT/JP2005/019626.
US Notice of Allowance, dated Apr. 23, 2009, for U.S. Appl. No. 11/136,355.
US Notice of Allowance, dated Aug. 11, 2009, for U.S. Appl. No. 11/136,355.
US Notice of Allowance, dated Dec. 23, 2008, for U.S. Appl. No. 11/136,355.
US Notice of Allowance, dated Mar. 11, 2010 for U.S. Appl. No. 11/878,556.
US Notice of Allowance, dated Nov. 4, 2009, for U.S. Appl. No. 12/497,251.
US Notice of Allowance, dated Sep. 27, 2010, for U.S. Appl. No. 12/721,952.
US Office Action, dated Apr. 22, 2010, for U.S. Appl. No. 11/596,723.
US Office Action, dated Feb. 28, 2008, for U.S. Appl. No. 11/136,355.
US Office Action, dated Jul. 2, 2009, for U.S. Appl. No. 11/596,723.
US Office Action, dated Jul. 6, 2010, for U.S. Appl. No. 11/596,723.
US Office Action, dated Oct. 26, 2009, for U.S. Appl. No. 11/596,723.
Horig et al., "From bench to clinic and back: Perspective on the 1st IQPC Translational Research Conference," Journal of Translational Medicine 2004, vol. 2, No. 44.
Office Action issued Jan. 11, 2011, in copending U.S. Appl. No. 12/522,281.
Office Action issued Jan. 24, 2011, in copending U.S. Appl. No. 12/301,428.
Office Action issued Nov. 12, 2010, in Chinese Patent Application No. 200780018090.5 (with English translation).
Schafer et al., "Failure is an option: learning from unsuccessful proof-of-concept trials," Drug Discovery Today 2008, vol. 13, Nos. 21/22, pp. 913-916.

* cited by examiner

AMORPHOUS OBJECT OF CINNAMIDE COMPOUND

TECHNICAL FIELD

The present invention relates to an amorphous substance of a cinnamide compound having an amyloid β production-reducing effect. More specifically, the present invention relates to an amorphous substance of a cinnamide compound as a novel compound, having favorable physical properties such as excellent solubility, no easy transition to a crystalline form, and low hygroscopicity.

BACKGROUND ART

Alzheimer's disease is a disease characterized by the degeneration or deciduation of nerve cells as well as the formation of senile plaques and the change of neurofibrils. The treatment of Alzheimer's disease is currently limited to symptomatic therapy using a symptom-improving agent exemplified by an acetylcholinesterase inhibitor; a basic therapeutic agent inhibiting the progression of the disease has not been developed. For creating a causal therapeutic agent for Alzheimer's disease, a method for controlling the pathogenesis of the disease state needs to be developed.

Aβ protein, a metabolic product of amyloid precursor protein (hereinafter referred to as APP), is thought to be significantly involved in the degeneration and deciduation of nerve cells and further the onset of dementia symptoms (see, for example, non-patent documents 1 and 2). The major components of Aβ protein are Aβ40 consisting of 40 amino acids and Aβ42 containing additional 2 amino acids. It is known that the Aβ40 and Aβ42 have high aggregability (see, for example, non-patent document 3) and are major constituents of the senile plaque (see, for example, non-patent documents 3, 4, and 5) and further that mutations in APP and presenilin genes seen in familial Alzheimer's disease increase the Aβ40 and Aβ42 (see, for example, non-patent documents 6, 7, and 8). Thus, a compound reducing the production of Aβ40 and Aβ42 is expected as an agent inhibiting the progression of, or preventing Alzheimer's disease.

Non-patent document 1: Klein W L and 7 coauthors, Alzheimer's disease-affected brain: Presence of oligomeric Aβ ligands (ADDLs) suggests a molecular basis for reversible memory loss, Proceeding National Academy of Science USA, 2003, Sep. 2; 100(18): 10417-10422.

Non-patent document 2: Nitsch R M and 16 coauthors, Antibodies against β-amyloid slow cognitive decline in Alzheimer's disease, Neuron, 2003, May 22; 38: 547-554.

Non-patent document 3: Jarrett J T and 2 coauthors, The carboxy terminus of the β amyloid protein is critical for the seeding of amyloid formation: Implications for the pathogenesis of Alzheimers' disease, Biochemistry, 1993, 32(18): 4693-4697.

Non-patent document 4: Glenner G G and 1 coauthor, Alzheimer's disease: initial report of the purification and characterization of a novel cerebrovascular amyloid protein, Biochemical and biophysical research communications, 1984, May 16, 120(3): 885-890.

Non-patent document 5: Masters C L and 5 coauthors, Amyloid plaque core protein in Alzheimer disease and Down syndrome, Proceeding National Academy of Science USA, 1985, June, 82(12): 4245-4249.

Non-patent document 6: Gouras G K and 11 coauthors, Intraneuronal Aβ42 accumulation in human brain, American Journal of Pathology, 2000, January, 156(1): 15-20.

Non-patent document 7: Scheuner D and 20 coauthors, Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2(8): 864-870.

Non-patent document 8: Forman M S and 4 coauthors, Differential effects of the swedish mutant amyloid precursor protein on β-amyloid accumulation and secretion in neurons and nonneuronal cells, The Journal of Biological Chemistry, 1997, Dec. 19, 272(51): 32247-32253.

DISCLOSURE OF THE INVENTION

Problems to be Solved by the Invention

The present inventors have found (3E)-1-[(1S)-1-(4-fluorophenyl)ethyl]-3-[3-methoxy-4-(4-methyl-1H-imidazol-1-yl)benzylidene]piperidin-2-one represented by formula (1) below:

[Formula 1]

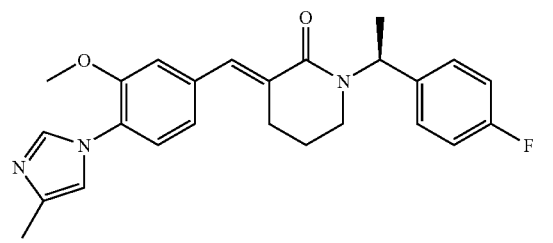

(1)

as a novel compound, the compound being one of typical cinnamide compounds which are excellent in the effect of reducing the production of amyloid Aβ40 and Aβ42 and expected as therapeutic and prophylactic agents for neurodegenerative diseases such as Alzheimer's disease.

On the other hand, the physical properties of a compound useful as a medicine and its salts and crystalline and amorphous substances thereof have a large influence on medicine bioavailability, bulk medicine purity, the formulation of preparations, and the like; therefore, it is necessary to study which salt, crystal form, or amorphous substance of the compound is most excellent as a medicine. Thus, because their physical properties depend on the attributes of an individual compound, it is generally difficult to predict a salt, crystal form, or amorphous substance thereof for use in a bulk medicine, having favorable physical properties; various studies need to be actually carried out for each compound.

Means for Solving the Problem

The present inventors have isolated various salts, crystal forms, and amorphous substances of (3E)-1-[(1S)-1-(4-fluorophenyl)ethyl]-3-[3-methoxy-4-(4-methyl-1H-imidazol-1-yl)benzylidene]piperidin-2-one, a novel compound expected as a therapeutic and prophylactic agent for neurodegenerative diseases such as Alzheimer's disease, followed by determining the physical properties and morphologies thereof for various studies. As a result, the inventors have found that an amorphous substance of a novel free form of the compound has favorable physical properties such as excellent solubility, no easy transition to a crystalline form, and low hygroscopicity, and is useful as a bulk medicine, thereby accomplishing the present invention.

Effects of the Invention

Thus, the present invention relates to an amorphous compound of (3E)-1-[(1S)-1-(4-fluorophenyl)ethyl]-3-[3-methoxy-4-(4-methyl-1H-imidazol-1-yl)benzylidene]piperidin-2-one.

Preferably, the present invention relates to an amorphous compound of (3E)-1-[(1S)-1-(4-fluorophenyl)ethyl]-3-[3-methoxy-4-(4-methyl-1H-imidazol-1-yl)benzylidene]piperidin-2-one, containing no crystalline form.

Preferably, the present invention also relates to an amorphous compound of (3E)-1-[(1S)-1-(4-fluorophenyl)ethyl]-3-[3-methoxy-4-(4-methyl-1H-imidazol-1-yl)benzylidene]piperidin-2-one, having no diffraction peak detected by powder X-Ray diffraction.

In addition, the present invention also relates to methods wherein (3E)-1-[(1S)-1-(4-fluorophenyl)ethyl]-3-[3-methoxy-4-(4-methyl-1H-imidazol-1-yl)benzylidene]piperidin-2-one is made in the form of an amorphous substance for increasing the solubility of the compound.

Further, the present invention also relates to methods wherein (3E)-1-[(1S)-1-(4-fluorophenyl)ethyl]-3-[3-methoxy-4-(4-methyl-1H-imidazol-1-yl)benzylidene]piperidin-2-one is made in the form of an amorphous substance for reducing the chargeability of the compound.

The present invention has made it possible to obtain an amorphous substance of (3E)-1-[(1S)-1-(4-fluorophenyl)ethyl]-3-[3-methoxy-4-(4-methyl-1H-imidazol-1-yl)benzylidene]piperidin-2-one. The amorphous substance of the compound has favorable physical properties such as excellent solubility and stability, no easy transition to a crystalline form, and low hygroscopicity, and is suitable for formulation.

Figure 1:
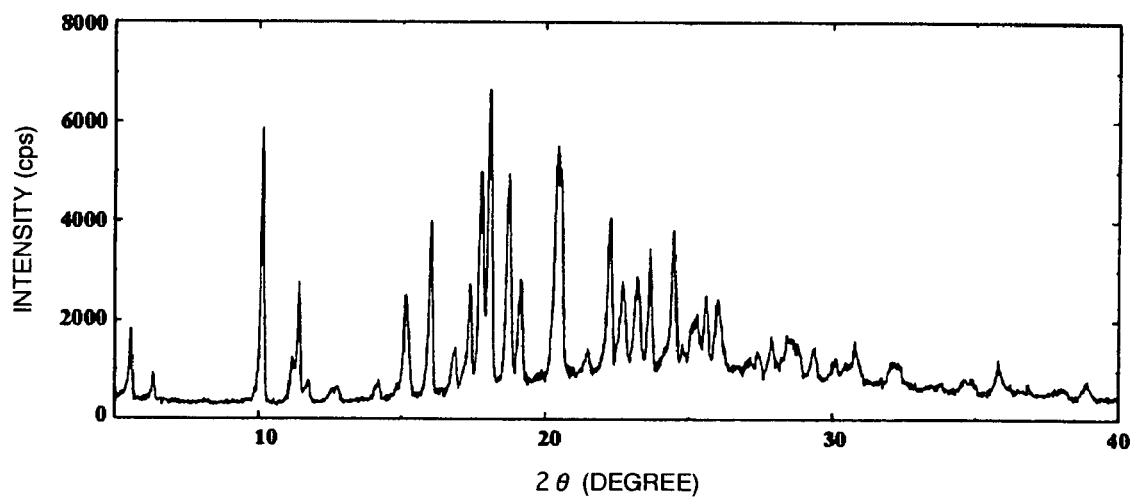
FIG. 1 is an X-ray diffraction pattern of a crystalline substance of (3E)-1-[(1S)-1-(4-fluorophenyl)ethyl]-3-[3-methoxy-4-(4-methyl-1H-imidazol-1-yl)benzylidene]piperidin-2-one obtained in (5) of Reference Example 1. The horizontal axis represents a diffraction angle (2θ), and the ordinate axis represents peak intensity.

A method for producing the novel compound of the present invention as a cinnamide compound and methods for producing and drying an amorphous substance thereof are described below in detail.

The novel compound of the present invention, (3E)-1-[(1S)-1-(4-fluorophenyl)ethyl]-3-[3-methoxy-4-(4-methyl-1H-imidazol-1-yl)benzylidene]piperidin-2-one (hereinafter, sometimes abbreviated as compound (1)) can be produced using, for example, synthesis methods described in detail in Reference Examples 1 and 2. That is, the novel compound of the present invention can be produced, for example, by using tertiary-butyl 5-chloro-2-(diethoxyphosphoryl)valerate in (1) of Reference Example 1 as a starting compound to react the starting compound with a compound obtained in Reference Example 2 to synthesize tertiary-butyl (3E)-5-chloro-2-[3-methoxy-4-(4-methyl-1H-imidazol-1-yl)benzylidene]valerate in (2) of Reference Example 1, from which the protecting group is then removed to synthesize (3E)-5-chloro-2-[3-methoxy-4-(4-methyl-1H-imidazol-1-yl)benzylidene]valeric acid trifluoroacetate in (3) of Reference Example 1 before making (3E)-5-chloro-2-[3-methoxy-4-(4-methyl-1H-imidazol-1-yl)benzylidene]valeric acid [(S)-1-(4-fluorophenyl)ethyl]amide in (4) of Reference Example 1, followed by subjecting this compound to ring closure reaction as described in (5) of Reference Example 1.

Methods for producing and drying the amorphous substance of the present invention are described below in detail.

A Method for Producing the Amorphous Substance

For producing the amorphous substance of the compound (1) of the present invention, a general method for producing an amorphous substance is adopted. Specifically, the amorphous substance can be produced, for example, by dissolving, in methanol or the like, the compound (1) produced according to the synthesis method described in Reference Example 1, followed by distilling off the solvent under reduced pressure.

The compound (1) used may be a hydrate or an anhydride, or may be an amorphous substance or comprise a crystalline substance having one crystal form or a crystalline substance having polymorphs, or may be a mixture thereof.

Examples of the solvent used can include an alkyl ketonic solvent such as acetone and 2-butane; ethyl acetate; hexane; acetonitrile; an alcoholic solvent such as ethanol, 1-propanol, and isopropanol; an organic solvent such as N,N-dimethylformamide; water; and a mixed solvent of two kinds or more thereof. More preferred examples thereof include ethyl acetate, acetonitrile, methanol, and ethanol.

The usage amount of the solvent may be properly selected from amounts corresponding to and exceeding the lower limit determined by the amount thereof allowing the compound (1) to be dissolved by heating, but preferably it is, for example, an amount corresponding to a ratio of the volume thereof to the weight of the compound (1) of 5 to 50 (v/w). The amount of the solvent used is preferably, for example, an amount corresponding to 5 to 30 (v/w), and, when methanol is employed as a solvent, more preferably an amount corresponding to the ratio of about 10 (v/w).

The temperature at which the compound (1) is dissolved by heating may be a temperature at which the compound (1) is dissolved, properly selected depending on the solvent, but preferably, for example, 15° C. to the reflux temperature of the solvent, more preferably, for example, 30 to 60° C.

In that way, the compound (1) can be dissolved in a solvent, followed by distilling off the solvent under reduced pressure to produce the amorphous substance of the compound (1).

In like manner, for example, one solvent selected from the group consisting of dimethylformamide, dimethylsulfoxide, and water or a mixed solvent of two or more of the solvents can be also used for freeze drying or spray drying to provide the amorphous substance of the compound (1).

The amorphous substance of the compound (1) obtained as described above has favorable physical properties such as excellent solubility and stability, no easy transition to a crystalline form, and low hygroscopicity, and is suitable for formulation. Thus, the amorphous substance of the compound (1) thus obtained may be subjected to formulation as it is, or may be formulated after drying by a drying method described below.

A Method for Drying the Amorphous Substance

The amorphous substance may be dried by allowing to stand in the air or heating, as needed.

The drying time may be a time before the residual solvents becoming down from a predetermined amount, properly selected depending on the amount of production, the drying device, the drying temperature, and the like. The drying may be carried out under ventilation or under reduced pressure. The degree of decompression may be properly selected depending on the amount of production, the drying device, the drying temperature, and the like. The resultant amorphous substance may be, if necessary, also allowed to stand in the air after drying.

The amorphous substance of the compound (1) obtained by the above-described drying method has favorable physical properties such as excellent stability, no easy transition to a crystalline form, and low hygroscopicity, and is also suitable for formulation.

The amorphous substance of the compound (1) of the present invention preferably does not contain any crystalline forms, but may partially contain the crystalline forms; the amorphous substance is preferably contained in an amount of at least 80 weight %, more preferably at least 90 weight %.

In addition, the amorphous substance of the compound (1) of the present invention preferably has no diffraction peak detected by powder X-Ray diffraction.

As is clear from the above description, the increased solubility of the compound (1) can be achieved by making the compound in the form of an amorphous substance using the above-described methods for producing and drying an amorphous substance. As used herein, the solubility of the compound (1) refers to the solubility thereof, for example, in water, a halogenic organic solvent such as carbon tetrachloride, dichloromethane, and chloroform, an etheric organic solvent such as 1,4-dioxane, tetrahydrofuran, 1,2-dimethoxyethane, methyl t-butyl ether, cyclopentyl methyl ether, diethyl ether, diisopropyl ether, dibutyl ether, and dichloropentyl ether, an amidic organic solvent such as N,N-dimethylformamide and N-methylpyrrolidone, an aromatic hydrocarbonic organic solvent such as benzene, toluene, and xylene, an aliphatic hydrocarbonic organic solvent such as heptane and hexane, an alcoholic organic solvent such as methanol, ethanol, and propanol, an esteric organic solvent such as methyl acetate and ethyl acetate, or a nitrilic organic solvent such as acetonitrile.

The reduced chargeability of the compound (1) can be also achieved by making the compound in the form of an amorphous substance using the above-described methods for producing and drying an amorphous substance.

The compound (1) has the effect of reducing the production of Aβ, and can be used as an active ingredient of therapeutic agents for neurodegenerative diseases attributable to Aβ such as, for example, Alzheimer's disease and Down's disease. Thus, when the amorphous substance of the compound (1) is used as a medicine, it is orally or parenterally administered as a therapeutic agent, for example, for neurodegenerative diseases attributable to Aβ such as, for example, Alzheimer's disease and Down's disease. The dosage thereof varies depending, for example, on the degree of symptoms, the age, sex, and body weight of a patient, sensitivity difference, the method, period, and interval of administration, the properties, preparation, and type of a pharmaceutical formulation, and the kind of an active ingredient, and is not particularly limited, but it is typically, for example, 10 to 6,000 mg, preferably about 50 to 4,000 mg, more preferably about 100 to 3,000 mg per day per adult which is typically given in 1 to 3 divided portions.

When an oral solid dosage form is prepared, an excipient and, as needed, additives such as a binder, a disintegrator, a lubricant, a colorant, and a flavoring agent are added to a base, which is then made in the form of, for example, a tablet, a coated tablet, a granule, a fine granule, a powder, or a capsule using an ordinary method. By way of example, lactose, corn starch, saccharose, glucose, sorbit, crystalline cellulose, or silicon dioxide is used as an excipient; polyvinyl alcohol, ethyl cellulose, methyl cellulose, gum arabic, hydroxypropylcellulose, or hydroxypropyl methylcellulose, as a binder; magnesium stearate, talc, or silica, as a lubricant; a colorant the addition of which to medicines is approved, as a colorant; and powdered cocoa, menthol, aromatic acid, peppermint oil, Borneo camphor, and powdered cinnamon bark, as a flavoring agent. Off course, the tablet and granule are allowed to be properly subjected to coating with sugar, gelatin, and other coatings, as needed. When an injection is prepared, additives such as, for example, a pH adjustor, a buffer, a suspending agent, a solubilizer, a stabilizer, an isotonizing agent, and a preservative are added as needed, for example, to make an intravenous, subcutaneous, or intramuscular injection using an ordinary method. In this instance, the injection may be made in the form of a freeze-dried product as needed. Examples of the suspending agent include methyl cellulose, polysorbate 80, hydroxyethyl cellulose, gum arabic, powdered tragacanth, sodium carboxymethylcellulose, and polyoxyethylene sorbitan monolaurate.

BEST MODE FOR CARRYING OUT THE INVENTION

The present invention is described below in detail with reference to Reference Examples, Example, and Test Examples. However, the present invention is not intended to be limited to these examples.

The following abbreviations are used in Reference Examples and Example below.

DMF: N,N'-dimethylformamide
THF: tetrahydrofuran
EDC: 1-ethyl-3-(3-dimethylaminopropyl)-carbodiimide hydrochloride
HOBT: 1-hydroxybenzotriazole
IPEA: diisopropylethylamine Reference Example 1

Synthesis of (3E)-1-[(1S)-1-(4-fluorophenyl)ethyl]-3-[3-methoxy-4-(4-methyl-1H-imidazol-1-yl)benzylidene]-piperidin-2-one

[Formula 2]

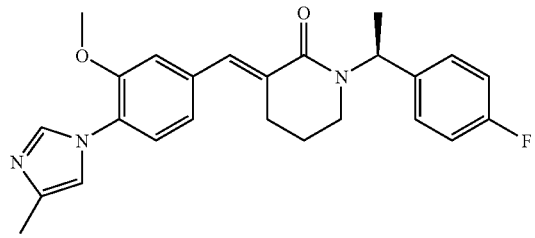

(1) Synthesis of tertiary-butyl 5-chloro-2-(diethoxyphosphoryl)valerate

Sodium hydride (containing 40% mineral oil, 17.4 g) was washed thrice with hexane (100 mL) to remove an oily substance. A THF (100 mL) solution of tertiary-butyl diethylphosphonoacetate (100 g) was added dropwise to a THF (500 mL) suspension of the sodium hydride at 0° C. over a period of 30 minutes. Subsequently, the reaction liquid was heated up to room temperature, and further stirred for one hour. A THF (100 mL) solution of 1-bromo-3-chloropropane (125 g) was added dropwise to the reaction solution over a period of 30 minutes. After the end of dropwise addition, the reaction liquid was heated to reflux for 15 hours. This reaction solution was allowed to stand to cool to room temperature, to which ethyl acetate (1 L) and a saturated ammonium chloride aqueous solution (1 L) were then added to separate an organic layer. The resultant organic layer was dried with anhydrous magnesium sulfate, and concentrated under reduced pressure to provide 113.4 g of the title compound. The physical property values of this compound are as follows.

$^1$H-NMR (CDCl$_3$) δ (ppm): 1.31-1.48 (m, 6H), 1.48 (s, 9H), 1.79-2.14 (m, 4H), 2.73-2.91 (m, 1H), 3.55 (t, J=6.4 Hz, 2H), 4.10-4.19 (m, 4H).

(2) Synthesis of tertiary-butyl (3E)-5-chloro-2-[3-methoxy-4-(4-methyl-1H-imidazol-1-yl)benzylidene]-valerate To a solution of 3-methoxy-4-(4-methyl-1H-imidazol-1-yl)benzaldehyde (50 g) obtained in Reference Example 2 in THF (600 mL) and ethanol (200 mL) were sequentially added tertiary-butyl 5-chloro-2-(diethoxyphosphoryl)valerate (83.5 g) and lithium hydroxide monohydrate (29.1 g), and the reaction liquid was stirred overnight at room temperature. After confirming the disappearance of the raw materials, water and ethyl acetate were added to the reaction liquid to separate an organic layer. The resultant organic layer was washed with saturated saline, dried with anhydrous magnesium sulfate, and concentrated under reduced pressure. The residue was purified using silica gel chromatography (elution solvent: heptane:ethyl acetate=1:1), followed by recrystallizing the resultant solid matter from a mixed solution of ethyl acetate and hexane to provide 54.9 g of the title compound. The physical property values of this compound are as follows.

$^1$H-NMR (CDCl$_3$) δ (ppm): 1.55 (s, 9H), 1.99-2.08 (m, 2H), 2.30 (s, 3H), 2.63-2.71 (m, 2H), 3.59 (t, J=6.4 Hz, 2H), 3.87 (s, 3H), 6.93 (m, 1H), 7.00 (d, J=1.2 Hz, 1H), 7.09 (dd, J=8.4, 1.2 Hz, 1H), 7.27 (d, J=8.4 Hz, 1H), 7.58 (s, 1H), 7.72 (m, 1H).

(3) Synthesis of (3E)-5-chloro-2-[3-methoxy-4-(4-methyl-1H-imidazol-1-yl)benzylidene]valeric acid trifluoroacetate Trifluoroacetic acid (10 mL) was added to a methylene chloride (20 mL) solution of tertiary-butyl (3E)-5-chloro-2-[3-methoxy-4-(4-methyl-1H-imidazol-1-yl)benzylidene] valerate (5 g), and the reaction liquid was stirred at room temperature for 2 hours. After confirming the disappearance of the raw materials, the reaction liquid was concentrated under reduced pressure, and the resultant solid matter was collected by filtration and further washed with ethyl acetate to provide 5.7 g of the title compound. The physical property values of this compound are as follows.

$^1$H-NMR (DMSO-d$_6$) δ (ppm): 1.93-2.03 (m, 2H), 2.35 (s, 3H), 2.58-2.66 (m, 2H), 3.70 (t, J=6.4 Hz, 2H), 3.91 (s, 3H), 7.24 (dd, J=8.4, 1.2 Hz, 1H), 7.37 (d, J=1.2 Hz, 1H), 7.64 (d, J=8.4, 1H), 7.66 (m, 1H), 7.76 (s, 1H), 9.36 (m, 1H).

(4) Synthesis of (3E)-5-chloro-2-[3-methoxy-4-(4-methyl-1H-imidazol-1-yl)benzylidene]valeric acid [(S)-1-(4-fluorophenyl)ethyl]amide IPEA (12.4 mL), EDC (6.82 g) and HOBT (4.81 g) were sequentially added to a DMF (50 mL) solution of the resultant 5-chloro-2-[3-methoxy-4-(4-methyl-1H-imidazol-1-yl)benzylidene]valeric acid trifluoroacetate (8.00 g) and (S)-1-(4-fluorophenyl)ethylamine (2.60 g), and the reaction liquid was stirred overnight at room temperature. After confirming the disappearance of the raw materials, the solvent was concentrated under reduced pressure, followed by adding water and ethyl acetate to the residue to separate an organic layer. The organic layer was washed with saturated saline, dried with anhydrous magnesium sulfate, and concentrated under reduced pressure. The resultant residue was purified using silica gel chromatography (elution solvent: heptane:ethyl acetate=2:3→1:1→ethyl acetate) to provide 3.90 g of the title compound. The physical property values of this compound are as follows.

$^1$H-NMR (CDCl$_3$) δ (ppm): 1.56 (d, J=6.8 Hz, 3H), 1.95-2.02 (m, 2H), 2.30 (s, 3H), 2.70-2.74 (m, 2H), 3.58 (t, J=6.0 Hz, 2H), 3.85 (s, 3H), 5.17-5.24 (m, 1H), 6.15 (d, J=6.8 Hz, 1H), 6.92-6.96 (m, 3H), 7.02-7.07 (m, 2H), 7.17 (s, 1H), 7.23-7.25 (m, 1H), 7.32-7.36 (m, 2H), 7.70-7.71 (s, 1H).

(5) Synthesis of (3E)-1-[(S)-1-(4-fluorophenyl) ethyl]-3-[3-methoxy-4-(4-methyl-1H-imidazol-1-yl) benzylidene]-piperidin-2-one Sodium hydride (containing 40% mineral oil, 410 mg) was added to a DMF (30 mL) solution of (3E)-5-chloro-2-[3-methoxy-4-(4-methyl-1H-imidazol-1-yl)benzylidene]valeric acid [(S)-1-(4-fluorophenyl)ethyl]amide (3.90 g) at 0° C., and the reaction liquid was heated up to room temperature and then stirred overnight. After confirming the disappearance of the raw materials, the reaction liquid was cooled down to 0° C., to which water and ethyl acetate were then added to separate an organic layer. The resultant organic layer was washed with saturated saline, dried with anhydrous magnesium sulfate, and concentrated under reduced pressure. The residue was purified using silica gel chromatography (elution solvent: ethyl acetate→ethyl acetate:ethanol 10:1). The resultant solid matter was washed with diethyl ether, and further recrystallized from ethyl acetate to provide 2.60 g of the title compound. The physical property values of this compound are as follows.

$^1$H-NMR (CDCl$_3$) δ (ppm): 1.50 (d, J=7.2 Hz, 3H), 1.65-1.74 (m, 1H), 1.78-1.87 (m, 1H), 2.30 (s, 3H), 2.71-2.85 (m, 2H), 2.91-2.97 (m, 1H), 3.24 (ddd, J=3.6, 8.8, 12.0 Hz, 1H), 3.86 (s, 3H), 6.23 (q, J=7.2 Hz, 1H), 6.93 (t, J=1.2 Hz, 1H), 7.00-7.06 (m, 4H), 7.24-7.26 (m, 1H), 7.31-7.34 (m, 2H), 7.72 (d, J=1.2 Hz, 1H), 7.89 (s, 1H).

Reference Example 2

Synthesis of 3-methoxy-4-(4-methyl-1H-imidazol-1-yl)benzaldehyde (1) Synthesis of 3-methoxy-4-(4-methyl-1H-imidazol-1-yl)benzaldehyde and 3-methoxy-4-(5-methyl-1H-imidazol-1-yl)benzaldehyde Potassium carbonate (4.05 g) was added to a DMF (50 mL) solution of 4-fluoro-3-methoxybenzaldehyde (3.00 g) and 4-methylimidazole (3.307 g), and the reaction liquid was stirred overnight at 100° C. The resultant reaction mixture was concentrated under reduced pressure, followed by adding water and ethyl acetate to the residue to separate an organic layer. The organic layer was washed with saturated saline, dried with anhydrous magnesium sulfate, and concentrated under reduced pressure. The residue was purified using silica gel column chromatography (elution solvent: a hexane-ethyl acetate system) to provide 3-methoxy-4-(4-methyl-1H-imidazol-1-yl)benzaldehyde (856 mg) and 3-methoxy-4-(5-methyl-1H-imidazol-1-yl)benzaldehyde (44 mg).

The physical property values of 3-methoxy-4-(4-methyl-1H-imidazol-1-yl)benzaldehyde are as follows.
$^1$HNMR (CDCl$_3$) δ (ppm): 2.31 (s, 3H), 3.97 (s, 3H), 7.02 (brs, 1H), 7.44 (d, J=8.0 Hz, 1H), 7.55 (dd, J=1.6 Hz, 8.0 Hz, 1H), 7.58 (d, J=1.6 Hz, 1H), 7.84 (brs, 1H), 10.00 (s, 1H).

The physical property values of 3-methoxy-4-(5-methyl-1H-imidazol-1-yl)benzaldehyde are as follows.
$^1$HNMR (CDCl$_3$) δ (ppm): 2.10 (s, 3H), 3.90 (s, 3H), 6.91 (brs, 1H), 7.40 (d, J=8.0 Hz, 1H), 7.50 (d, J=1.2 Hz, 1H), 7.57-7.59 (m, 1H), 7.84 (s, 1H), 10.05 (s, 1H).

Alternatively, 3-methoxy-4-(4-methyl-1H-imidazol-1-yl)benzaldehyde can be also synthesized by the following method.

(2) Synthesis of methyl 3-methoxy-4-nitrobenzoate

Methyl iodide (463 g) was added dropwise to a DMF (1 L) mixture of 3-hydroxy-4-nitrobenzoic acid (199 g) and potassium carbonate (450 g) at room temperature. The reaction liquid was stirred overnight at room temperature, to which methyl iodide (230 g) was further added, followed by additionally stirring the reaction liquid at room temperature for 6 hours. The reaction liquid was added to ice water, followed by collecting the precipitated solid by filtration. The resultant solid was dried overnight at 50° C. to provide 178 g of the title compound. The physical property values thereof agreed with reported values (CAS#5081-37-8).

(3) Synthesis of methyl 4-amino-3-methoxybenzoate

To a solution of methyl 3-methoxy-4-nitrobenzoate (150 g) in methanol (600 mL) and THF (300 mL) was added 10% palladium-carbon (a 50% water-containing product, 15 g), and the reaction liquid was stirred at 50° C. to 64° C. under a hydrogen pressure of 0.9 MPa for 6.5 hours. The reaction liquid was allowed to stand to cool to room temperature and then filtered on celite, followed by concentrating the resultant filtrate under reduced pressure to provide 134 g of the title compound. The physical property values thereof agreed with reported values (CAS#41608-64-4).

(4) Synthesis of methyl 4-formylamino-3-methoxybenzoate

Acetic anhydride (268 mL) was added dropwise to formic acid (401 mL) at room temperature, and the reaction liquid was stirred at room temperature for 40 minutes. A THF (600 mL) solution of methyl 4-amino-3-methoxybenzoate (134 g) was added dropwise to the reaction liquid at room temperature, and the resultant reaction liquid was stirred for one hour. To the reaction liquid was added 3.8 L of ice water, and the precipitated solid was collected by filtration and further washed with water (2 L). The resultant solid was dried overnight at 50° C. to provide 111 g of the title compound. The physical property values thereof agreed with reported values (CAS#700834-18-0).

(5) Synthesis of methyl 4-[formyl-(2-oxopropyl)amino]-3-methoxybenzoate

Chloroacetone (84.5 mL) was added dropwise to a DMF (497 mL) mixture of methyl 4-formylamino-3-methoxybenzoate (111 g), cesium carbonate (346 g), and potassium iodide (8.78 g) at room temperature, and the reaction liquid was stirred for 3 hours. Cesium carbonate (173 g) and chloroacetone (42.0 mL) were further added to the reaction liquid, which was then stirred at room temperature for 2 hours. Ice water and ethyl acetate were added to the reaction liquid to separate an organic layer. Ethyl acetate was added to the aqueous layer to separate an organic layer. The organic layers were combined, which was then washed with water and saturated saline in that order, followed by drying the resultant organic layer with anhydrous magnesium sulfate before concentrating the organic layer under reduced pressure. The residue was diluted with toluene, followed by concentrating the solution under reduced pressure. To the resultant residue were added tertiary-butyl methyl ether and heptane, and the precipitated solid was collected by filtration and washed with a heptane solution of 50% tertiary-butyl methyl ether. The resultant solid was air-dried overnight to provide 118 g of the title compound.
$^1$HNMR (CDCl$_3$) δ (ppm): 2.19 (s, 3H), 3.91 (s, 3H), 3.94 (s, 3H), 4.49 (s, 2H), 7.31 (d, J=8.0 Hz, 1H), 7.63 (d, J=2.0 Hz, 1H), 7.69 (dd, J=8.0, 2.0 Hz, 1H), 8.33 (s, 1H).

(6) Synthesis of methyl 3-methoxy-4-(4-methyl-1H-imidazol-1-yl)benzoate

An acetic acid (255 mL) solution of methyl 4-[formyl-(2-oxopropyl)amino]-3-methoxybenzoate (118 g) and ammonium acetate (172 g) was heat-stirred at 140° C. for one hour. After the completion of reaction, the reaction liquid was neutralized with aqueous ammonia under cooling with ice. Ethyl acetate was added to the reaction liquid to separate an organic layer. The resultant organic layer was dried with anhydrous magnesium sulfate and filtered on a silica gel pad, followed by concentrating the filtrate under reduced pressure. To the residue were added tertiary-butyl methyl ether and heptane, followed by collecting the precipitated solid by filtration before washing with a heptane solution of 50% tertiary-butyl methyl ether. The resultant solid was air-dried overnight to provide 68.4 g of the title compound. In addition, the crystallizing mother liquor was concentrated under reduced pressure, followed by purifying the residue using silica gel column chromatography (elution solvent: a heptane-ethyl acetate system) to provide 22.3 g of the title compound.
$^1$HNMR (CDCl$_3$) δ (ppm): 2.30 (s, 3H), 3.94 (s, 3H), 3.96 (s, 3H), 6.98 (brs, 1H), 7.32 (d, J=8.4 Hz, 1H), 7.71-7.73 (m, 2H), 7.79 (brs, 1H).

(7) Synthesis of 3-methoxy-4-(4-methyl-1H-imidazol-1-yl)benzaldehyde

A THF (45 mL) solution of pyrrolidine (18 mL) was added dropwise to a THF (60 mL) solution of sodium bis(2-methoxyethoxy)aluminium hydride (a 65% toluene solution, 56 mL) at −5° C. or lower over a period of 15 minutes. The reaction liquid was stirred at room temperature for one hour, to which a THF (15 mL) suspension of tertiary-butoxide (2.10 g) was then dropwise added at room temperature, followed by stirring the reaction liquid for 15 minutes. The reaction liquid was added dropwise to a THF (50 mL) solution of methyl 3-methoxy-4-(4-methyl-1H-imidazol-1-yl)benzoate (20 g)

under cooling with ice over a period of 30 minutes. The reaction liquid was stirred at room temperature for 2 hours, to which a 5N sodium hydroxide aqueous solution (150 mL) was then added dropwise. Ethyl acetate was added to the reaction liquid to separate an organic layer. The organic layer was washed with a saturated ammonium chloride aqueous solution and saturated saline in that order. The organic layer was dried with anhydrous magnesium sulfate and filtered on a silica gel pad, followed by concentrating the filtrate under reduced pressure. The residue was diluted with ethyl acetate, followed by collecting the precipitated solid by filtration. The resultant solid was air-dried overnight to provide 7.10 g of the title compound. In addition, the crystallizing mother liquor was concentrated under reduced pressure, followed by purifying the residue using silica gel column chromatography (elution solvent: a heptane-ethyl acetate-2-propanol system) to provide 2.65 g of the title compound.

Test Example 1

Powder X-Ray Diffraction of the Crystalline Substance

A sample of the crystalline substance of (3E)-1-[(1S)-1-(4-fluorophenyl)ethyl]-3-[3-methoxy-4-(4-methyl-1H-imidazol-1-yl)benzylidene]piperidin-2-one obtained in (5) of Reference Example 1 was placed on the sample stage of a powder X-ray diffractometer, and subjected to X-ray diffraction analysis under conditions described in Table 1 below.

A powder X-ray diffraction pattern of the crystalline substance is shown in FIG. 1.

TABLE 1

| Measurement Conditions | |
|---|---|
| Sample holder | Glass |
| Target | Copper |
| Detector | Scintillation counter |
| Tube voltage | 40 KV |
| Tube current | 200 mA |
| Slit | DS1/2°, RS0.3 mm, SS1/2° |
| Scanning speed | 5°/min |
| Sampling interval | 0.02° |
| Scanning range | 5 to 40° |
| Goniometer | Vertical goniometer |

Example 1

Production of an Amorphous Substance of (3E)-1-[(1S)-1-(4-fluorophenyl)ethyl]-3-[3-methoxy-4-(4-methyl-1H-imidazol-1-yl)benzylidene]piperidin-2-one In methanol (3 ml) was dissolved (3E)-1-[(1S)-1-(4-fluorophenyl)ethyl]-3-[3-methoxy-4-(4-methyl-1H-imidazol-1-yl)benzylidene]piperidin-2-one (300 mg) at 50° C., from which the solvent was then distilled off under reduced pressure using an evaporator, followed by further drying under reduced pressure using a vacuum pump to provide 300 mg of the title compound. They physical property values of this compound are as follows.

$^1$H-NMR (CDCl$_3$) δ (ppm): 1.50 (d, J=7.2 Hz, 3H), 1.65-1.74 (m, 1H), 1.78-1.87 (m, 1H), 2.30 (s, 3H), 2.71-2.85 (m, 2H), 2.91-2.97 (m, 1H), 3.24 (ddd, J=3.6, 8.8, 12.0 Hz, 1H), 3.86 (s, 3H), 6.23 (q, J=7.2 Hz, 1H), 6.93 (t, J=1.2 Hz, 1H), 7.00-7.06 (m, 4H), 7.24-7.26 (m, 1H), 7.31-7.34 (m, 2H), 7.72 (d, J=1.2 Hz, 1H), 7.89 (s, 1H).

Test Example 2

Powder X-Ray Diffraction of the Amorphous Substance

A sample of the amorphous substance obtained by the production method of Example 1 was placed on the sample stage of a powder X-ray diffractometer, and subjected to X-ray diffraction analysis under conditions described in Table 2 below.

Figure 2:
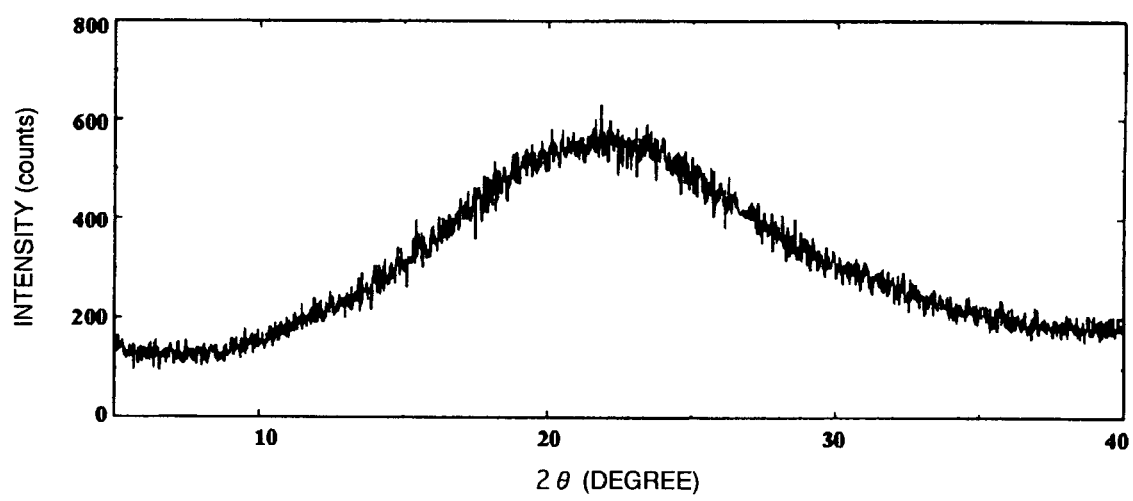
FIG. 2 is an X-ray diffraction pattern of an amorphous substance of (3E)-1-[(1S)-1-(4-fluorophenyl)ethyl]-3-[3-methoxy-4-(4-methyl-1H-imidazol-1-yl)benzylidene]piperidin-2-one obtained in Example 1. The horizontal axis represents a diffraction angle (2θ), and the ordinate axis represents peak intensity.

A powder X-ray diffraction pattern of the amorphous substance is shown in FIG. 2.

TABLE 2

| Measurement Conditions | |
|---|---|
| Sample holder | Glass |
| Target | Copper |
| Detector | Scintillation counter |
| Tube voltage | 40 KV |
| Tube current | 200 mA |
| Slit | DS1/2°, RS0.3 mm, SS1/2° |
| Scanning speed | 5°/min |
| Sampling interval | 0.02° |
| Scanning range | 5 to 40° |
| Goniometer | Vertical goniometer |

Test Example 3

Solubility Test of the Crystalline Compound (1) and the Amorphous Compound (1)

An excess amount of each sample was added to 0.5 mL of the following each test solution, which was then dispersed and dissolved by a ultrasonication operation for several minutes (about 3 minutes). After allowing to stand at room temperature for 30 minutes, the supernatant was separated by a centrifugation operation; the sample concentration in the supernatant as determined by an HPLC method was defined as an apparent solubility in each test solution.

pH 5: Diluted McIlvaine buffer solution (Kanto Chemical Co. Inc.)

pH 7: GIBCO™ (Dulbecco's phosphate-buffered saline, Invitrogen Corporation)

The solubilities of the amorphous compound (1) in the above buffers are shown in Table 3 below.

TABLE 3

| Solubility test results | | |
|---|---|---|
| Buffers | Test Samples | Apparent solubilites (mg/mL) |
| pH 5 buffer | Amorphous compound (1) | 0.225 |
| pH 5 buffer | Crystalline compound (1) | 0.077 |
| pH 7 buffer | Amorphous compound (1) | 0.011 |
| pH 7 buffer | Crystalline compound (1) | 0.003 |

The results in Table 3 demonstrate that the amorphous compound (1) had favorable solubilities compared to the crystalline compound (1).

Test Example 4

Hygroscopicity Test of the Amorphous Compound (1)

The hygroscopicity of the amorphous substance was evaluated using a microbalance (MB300W, VTI Corporation, USA). A sample placed in a glass holder was suspended in a device adjusted at 25° C., and a change in the weight thereof was followed over relative humidities of 5% to 90%. The sample weight was measured at measuring points (of the relative humidities) with an interval of 2 minutes; the weight at the time point of the amount of change reaching within 0.2% was defined as the final value.

Figure 3:
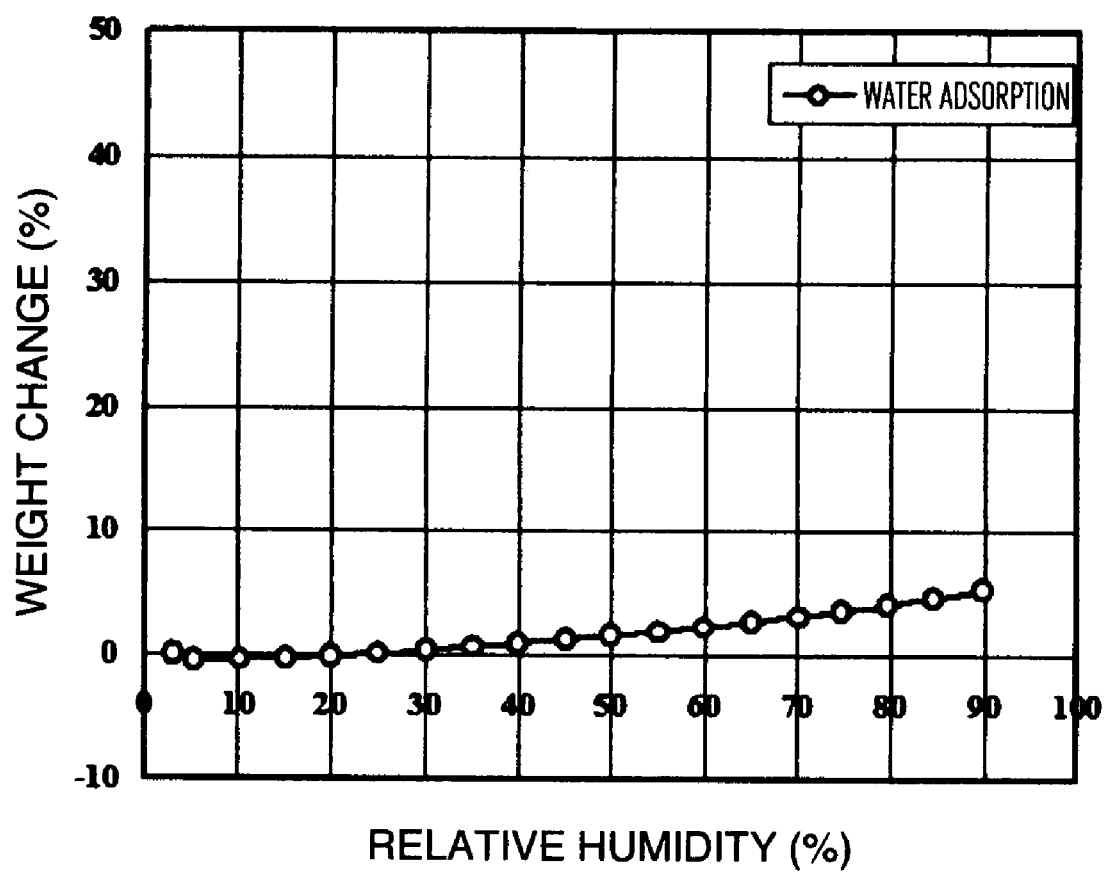
FIG. 3 is a hygroscopicity pattern of an amorphous substance of (3E)-1-[(1S)-1-(4-fluorophenyl)ethyl]-3-[3-methoxy-4-(4-methyl-1H-imidazol-1-yl)benzylidene]piperidin-2-one obtained in Example 1. The horizontal axis represents relative humidity (%), and the ordinate axis represents weight change (%).

A hygroscopicity pattern of the amorphous compound (1) is shown in FIG. 3. The hygroscopicity pattern in FIG. 3 demonstrates that the amorphous compound (1) had low hygroscopicity.

INDUSTRIAL APPLICABILITY

According to the present invention, there can be provided an amorphous substance of (3E)-1-[(1S)-1-(4-fluorophenyl)ethyl]-3-[3-methoxy-4-(4-methyl-1H-imidazol-1-yl)benzylidene]piperidin-2-one suitable for use in a medicinal preparation.

The invention claimed is:

1. An amorphous compound of (3E)-1-[(1S)-1-(4-fluorophenyl)ethyl]-3-[3-methoxy-4-(4-methyl-1H-imidazol-1-yl)benzylidene]piperidin-2-one made by:
   mixing (3E)-1-[(1S)-1-(4-fluorophenyl)ethyl]-3-[3-methoxy-4-(4-methyl-1H-imidazol-1-yl)benzylidene]piperidin-2-one with methanol;
   dissolving the (3E)-1-[(1S)-1-(4-fluorophenyl)ethyl]-3-[3-methoxy-4-(4-methyl-1H-imidazol-1-yl)benzylidene]piperidin-2-one by heating the mixture to 30 to 60° C.; and
   distilling off said methanol under reduced pressure, thereby producing said amorphous compound of (3E)-1-[(1S)-1-(4-fluorophenyl)ethyl]-3-[3-methoxy-4-(4-methyl-1H-imidazol-1-yl)benzylidene]piperidin-2-one.

2. The amorphous compound of claim 1, wherein said amorphous compound contains no crystalline form.

3. A method of making an amorphous compound of (3E)-1-[(1S)-1-(4-fluorophenyl)ethyl]-3-[3-methoxy-4-(4-methyl-1H-imidazol-1-yl)benzylidene]piperidin-2-one, said method comprising:
   mixing (3E)-1-[(1S)-1-(4-fluorophenyl)ethyl]-3-[3-methoxy-4-(4-methyl-1H-imidazol-1-yl)benzylidene]piperidin-2-one with methanol;
   dissolving the (3E)-1-[(1S)-1-(4-fluorophenyl)ethyl]-3-[3-methoxy-4-(4-methyl-1H-imidazol-1-yl)benzylidene]piperidin-2-one by heating the mixture to 30 to 60° C.; and
   distilling off said methanol under reduced pressure, thereby producing said amorphous compound of (3E)-1-[(1S)-1-(4-fluorophenyl)ethyl]-3-[3-methoxy-4-(4-methyl-1H-imidazol-1-yl)benzylidene]piperidin-2-one.

4. The method of claim 3, wherein the ratio of volume of the methanol to the weight of the 3E)-1-[(1S)-1-(4-fluorophenyl)ethyl]-3-[3-methoxy-4-(4-methyl-1H-imidazol-1-yl)benzylidene]piperidin-2-one compound is 5 to 30 (v/w).

* * * * *